United States Patent [19]

Finkle

[11] Patent Number: 5,338,288
[45] Date of Patent: Aug. 16, 1994

[54] NONINVASIVE MALE POTENCY DEVICE

[76] Inventor: Eugene Finkle, 48900 N. Hwy. 101/P.O. Box 309, Laytonville, Calif. 95454

[21] Appl. No.: 933,025

[22] Filed: Aug. 20, 1992

[51] Int. Cl.$^5$ .............................................. A61F 5/41
[52] U.S. Cl. ...................................................... 600/41
[58] Field of Search ................................. 600/38–39, 600/41; 606/203

[56] References Cited

U.S. PATENT DOCUMENTS

| 268,407 | 12/1882 | Hughes | 606/203 |
| 3,461,863 | 8/1969 | Sullinger | 600/41 |
| 5,027,800 | 7/1991 | Rowland | 600/39 |

FOREIGN PATENT DOCUMENTS 0158658  9/1954  Australia .............................. 600/41

*Primary Examiner*—Angela D. Sykes
*Attorney, Agent, or Firm*—Townsend and Townsend Khourie and Crew

[57] ABSTRACT

An apparatus for maintenance of a male erection-like state is provided. The invention includes a calibrated linear elastomeric constrictor adapted to be wrapped around a vacuum cylinder. Improvements in the vacuum apparatus include an aperture at a proximal region of the vacuum cylinder and a vacuum gauge. A skin surface temperature sensor is provided. The concomitant use of an electronic stimulation of the appropriate muscles is described to strengthen said muscles which are then used in conjunction with the device.

4 Claims, 2 Drawing Sheets

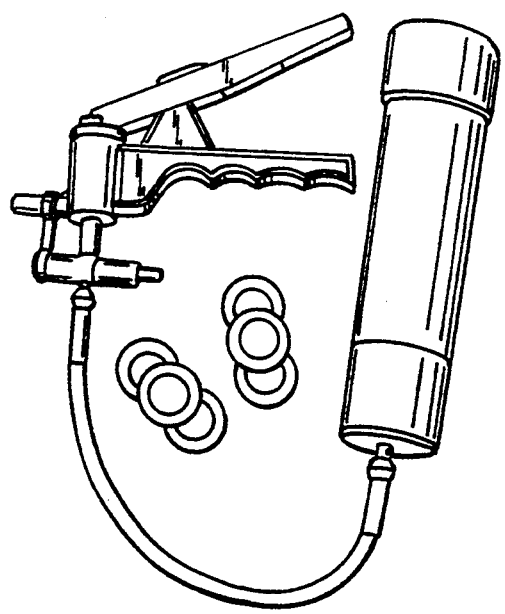
FIG. 1.
PRIOR ART
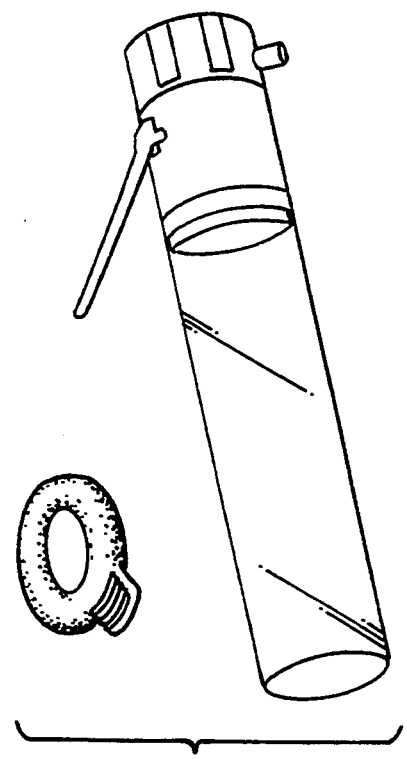
FIG. 2. PRIOR ART
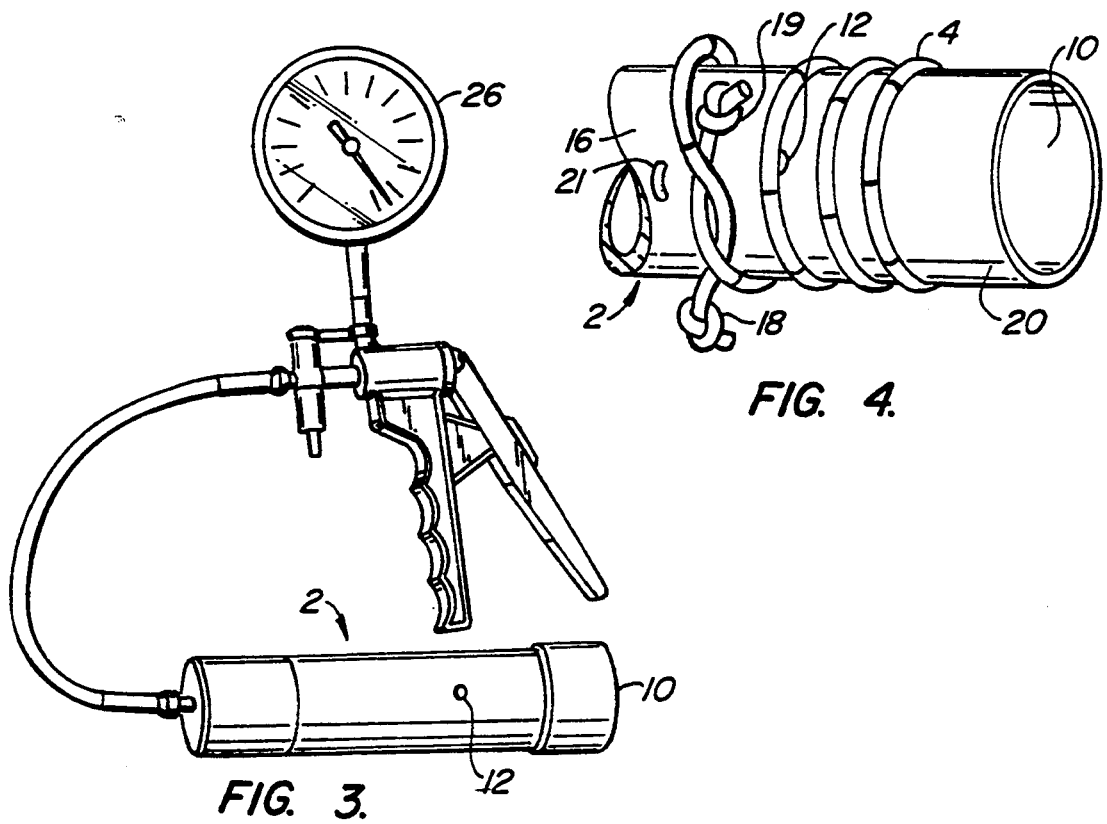
FIG. 3.
FIG. 4.

NONINVASIVE MALE POTENCY DEVICE

BACKGROUND OF THE INVENTION

The invention relates to production and maintenance of a male erection-like state. More specifically, the invention relates to a constriction means for use with a vacuum assisted device adaptable to different user requirements.

The prior art includes devices and methods for production and maintenance of a male erection-like state. These devices generally consist of three parts: a vacuum cylinder, a pump, and a constriction ring. For example, see U.S. Pat. No. 1,225,341 to Otto Lederer, issued in 1917 for a device which assists in producing an erection by creating a vacuum. A ring is included to maintain the erection. Another such device is disclosed in U.S. Pat. No. 4,856,498 to Osbon. A device including an elastomeric extensible ring is disclosed in U.S. Pat. No. 4,995,381 to Marmar et al.

The present state of the art constriction devices use a ring of some type. Some disadvantages associated with the ring include difficulty of removal, difficulty in customizing the pressure, and the risk of too much impedance of arterial flow and hypoxia or gangrene of the organ. Other problems include a reflex vasoconstriction if the vacuum is applied too rapidly. Additionally, ecchymoses and petechiae, small surface bruises on the skin, are problems associated with sudden vacuum application.

SUMMARY OF THE INVENTION

The invention includes a constrictor device which, when not in use, is a length of flat elastomeric material. Preferably the constrictor is calibrated with length markings either in inches or centimeters and knots are placed near each end. The constrictor is initially wrapped around a vacuum cylinder with a plurality of turns, and the distal knotted end is tucked underneath the proximal knotted end. After an erection is achieved, the user slips the constrictor off the cylinder and onto the base of the male organ. Following use the constrictor is easily removed by simply pulling on either end.

With a physiologic erection, detumescence occurs, but with the prior art vacuum device the erectile state is maintained by the constriction ring. Therefore if the conventional device is used, namely a fixed ring of some type, removal of the ring can be painful and difficult, in contrast to the present invention.

The invention also includes an improved vacuum generating device. The vacuum device has a small hole at its proximal portion, adjacent to the user's pelvis, which is useful for slow release of the vacuum. Additionally, a vacuum gauge is provided to permit incremental increase in application of the vacuum as well as reproducible and predictable amounts of vacuum application.

The vacuum tube is preferably calibrated with length markings which correspond to the length markings on the elastomeric constrictor device. That is, the markings are consistently either in centimeters or inches. Preferably, the vacuum tube includes elevations or a series of ridges adapted to receive the elastomeric constrictor. Other embodiments include a liquid crystal display (LCD) which detects the temperature of the penile skin. This surface temperature monitoring is useful for initial calibration and for length of time of vacuum application.

The entire apparatus can be used as a system when combined with an electronic stimulator to strengthen the bulbo-cavernosis and levator muscles in a pre-use training period. Said muscles are then contracted repeatedly when using the vacuum constricting device thereby producing a firmer erectile state.

Methods of use by the patient are included, as well as diagnostic applications.

BRIEF DESCRIPTION OF THE DRAWINGS

FIG. 1 shows a prior art vacuum and constriction rings.

FIG. 2 shows a prior art device including a one-piece vacuum cylinder and pump attachment and a constriction ring.

FIG. 3 shows an apparatus constructed in accordance with the present invention including a bleed-hole and vacuum gauge.

FIG. 4 shows an apparatus constructed in accordance with the present invention including a length of elastomeric constrictor wrapped around a vacuum tube with self locking feature.

DESCRIPTION OF THE PREFERRED EMBODIMENT

The present invention is a noninvasive device to produce and maintain an erection-like state. The device is based on two phenomena. One is that an erection-like state will occur when the male organ is placed in a vacuum. The other is that this state can be maintained by a constricting means placed about the base of the male organ. Under normal circumstances the organ becomes erect because of engorgement with blood. In the flaccid state the blood flow is in a steady state in which inflow equals outflow. With stimulation, there is a dilation of the arteries to the male organ which results in increased blood flow. Consequently, there is increased pressure inside the semi-rigid coating of the male organ or *tunicus albuginea*.

Poiseulle's Law of Fluid Flow states:

$$V = \frac{P \times \pi \times r^4}{n \times 1}$$

where P is pressure in dynes per square cm, $\pi$ is a constant, r is the tube radius, n is the coefficient of viscosity and 1 is the length of the vessels.

Poiseuille's Law states that fluid flow is directly proportional to pressure $\times$ radius$^4$ divided by length $\times$ viscosity. Since the arteries and veins will both be compressed and since the arterial wall is much thicker than the venous wall, the artery will compress less than the vein. Because blood flow is a function of the vessel's radius$^4$, the outflow must decrease more than the inflow and the organ becomes engorged and erect. As the pressure inside the organ increases, eventually a new steady state of blood flow will occur as long as the arteries remain dilated. This is because of the anatomy of the blood distribution channels inside the organ structure and Poiseuille's Law.

Some diseases, for example diabetes and arteriosclerosis, result in failure of erection. The common denominator among these diseases is a failure in the initial increase in arterial flow or a failure to decrease the outflow or a venous leakage. Vacuum devices create an erection-like state by increasing the mean arterial blood pressure to the organ and thus the blood flow. Pressure in the artery to the organ is the sum of the mean arterial pressure plus the atmospheric pressure, which is 760 mm of mercury (Hg).

In the flaccid state, atmospheric pressure is the same in the artery to the organ and in the organ. When a vacuum is applied to the organ, e.g. 200 mm Hg, the effective blood pressure to the organ becomes the mean arterial pressure plus the vacuum applied (200 mm Hg). This causes engorgement through the mechanism described above. When the vacuum is removed, the organ returns to the flaccid state because the arterial blood flow returns to the pre-vacuum state. In order to maintain the erection, a constriction device is applied to impede the outflow, thus compensating for the normal erectile state where the inflow is increased physiologically.

Figure 5A:
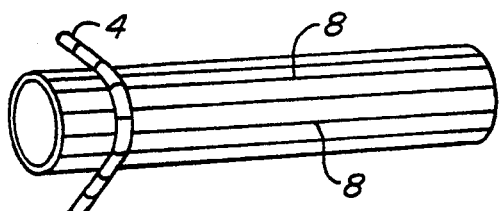
FIG. 5A shows an unknotted constrictor in accordance with the present invention.
Figure 6A:
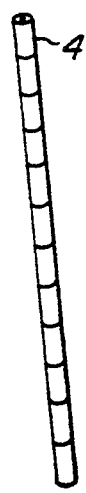
FIG. 6A shows a constrictor constructed in accordance with the present invention without knots.
Figure 6B:
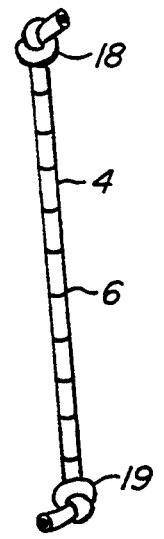
FIG. 6B shows a constrictor constructed in accordance with the present invention having calibration markings and knots or bulges on each end.
Figure 5B:
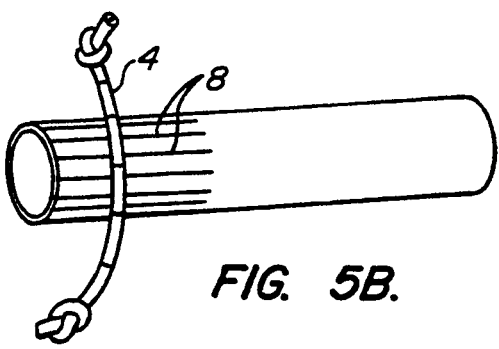
FIG. 5B shows a device constructed in accordance with the present invention including a vacuum tube having calibration marks which correspond to calibration marks on the constrictor device.

The invention includes a constrictor 4 which is a length of an elastomeric material which is generally elongated from the perspective of a plan view. See FIG. 6A. In a preferred embodiment, a length of about thirteen inches of one-eighth inch thick latex surgical tubing is used. Latex tubing is conveniently used as constrictor 4 because of its wide availability. However, a flat nontubular length of elastomeric material could be employed instead. The constrictor need not possess tubular construction. Preferably, constrictor 4 is provided with calibration marks 6 either in centimeters or inches and has a knot or bulge at either end 18, 19. See FIG. 6B.

In use, constrictor 4 is wrapped around a proximal portion 20 of a vacuum cylinder 2 a number of times, preferably about 3–5 turns. The pressure exerted by constrictor 4 is a function of the size of the male organ, the elasticity of constrictor 4 and the number of turns around cylinder 2. Constrictor 4 is preferably held in place by a distal knot on the last turn tucked under the proximal knot on the starting turn, thus being held in place by constrictor 4's own elasticity. FIG. 4. Although this self-retaining feature is preferred, other securing means could be used. The male organ is placed into cylinder 2 at a proximal opening 10.

In addition, a small projection 21 is provided on the proximal end of the vacuum cylinder 20 under which the proximal knot is placed to hold it steady for ease of application and reproducibility of the starting position.

When an erection is obtained using the vacuum, constrictor 4 is slipped off proximal end 20 of cylinder 2 onto the organ where it acts as a constricting ring. After use, constrictor 4 is easy to remove. Either knot end is simply pulled and constrictor 4 unties and slips off. Additionally, comfort is increased because of the wider base or width of the device. Also pressure may be varied infinitely. That is, given a base circumference of a male organ and a length of approximately one-eighth inch thick latex constrictor, the pressure can be varied by any of the following ways: (1) changing the length of constrictor 4 by appropriate placement of knots 18 and 19; (2) varying the elastic force of constrictor 4 by matching calibrations 6 against vacuum cylinder calibrations 8 which are constant; (3) varying the number of turns of constrictor 4 around vacuum cylinder 2; and (4) varying the elastomeric character of constrictor 4 using different thicknesses, shapes or type of material.

The length of constrictor 4 can be effectively changed by changing the location of knots 18 and 19. The pressure can be changed by changing the number of turns or loops of constrictor 4, and changing the elasticity by changing the length, size, geometry or elasticity of the linear constricting device. The changes in the above variables can be reproduced by use of calibration marks 6 on the constrictor and calibration marks 8 on the vacuum cylinder. The elasticity of the constrictor device 4 can also be reduced to prevent a snapping effect on application by filling it with an viscoelastic polymer, e.g. "silly putty," or alternatively threading through the center, if it is tubular shaped, a length of tubing of lesser elasticity.

Figure 7:
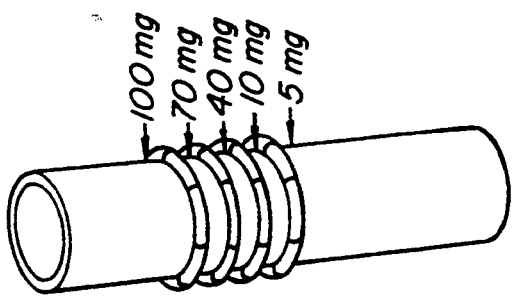
FIG. 7 shows a device constructed in accordance with the present invention indicating various incremental pressure changes which correspond to turns of the constrictor device in mm of Hg.

An additional advantage is increased safety against excess pressure and cutting off of the arterial blood flow. Safety is enhanced by the plurality of turns. Each turn allows less pressure and produces a series of pressure drops. In contrast to a constriction ring requiring enough pressure to produce the appropriate change in flow in one or, at most, two stages, the present device allows a gradual or incremental pressure variation. FIG. 7.

Figure 8:
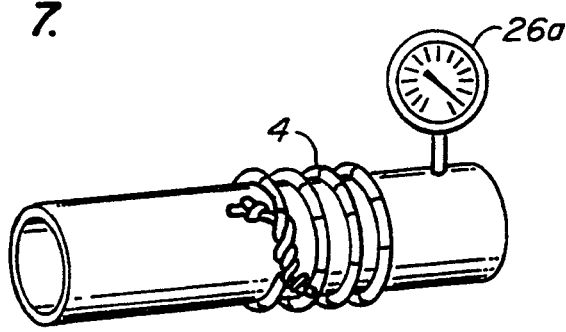
FIG. 8 shows a pressure gauge to calibrate the constriction device.

By altering the above variables, the pressure exerted by the easily released constriction device can be quantitated by use of a model male organ pressure transducer and pressure gauge 26a. FIG. 8. A calibration nomogram can be constructed for each organ size. An example of such a nomogram is displayed in Table I below, where the number of turns refers to the number of turns of the constrictor, mm refers to pressure in mm of Hg, and the lengths of 9, 10 and 11 inches refer to the length of the organ.

TABLE I

| A 9" length of ⅛" thick Surgical Latex Tubing | | | |
| --- | --- | --- | --- |
| Number of Turns | 9" | 10" | 11" |
| 2 | 10 mm | 8 mm | 6 mm |
| 3 | 15 mm | 13 mm | 11 mm |
| 4 | 20 mm | 18 mm | 16 mm |
| 5 | 25 mm | 23 mm | 21 mm |

The pressure inside the male organ with erection exceeds systolic arterial pressure because of the constriction of the bulbo-cavernosis and levator muscles. Another feature the present device can provide is a pre-use training period for increasing the strength of the above muscles by electronic device stimulation and repetitive voluntary contractions of said muscles. Such electronic stimulators are in common use for the treatment of urinary and fecal incontinence. After pre-use training and strengthening the above muscles can be intermittently, voluntarily contracted while the vacuum is being applied to produce a much more rigid erectile state.

Preferably, a small hole 12 is placed at proximal portion 20 of vacuum cylinder 2. See FIG. 3. Measuring about one-sixteenth inch in diameter, hole 12 is covered by constrictor 4 while maintaining the vacuum. As constrictor 4 is slipped off cylinder 2 and onto the male organ, the vacuum is gradually released from cylinder 2 through hole 12. This allows an easier removal of vacuum cylinder 2 and a firmer erection-like state. Alternatively, hole 12 could be taped or plugged instead of blocked by constrictor 4. Coordination of constriction and vacuum removal permits an optimum maintenance of rigidity.

Figure 6C:
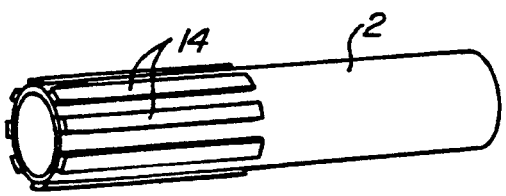
FIG. 6C shows a vacuum cylinder constructed in accordance with the present invention having longitudinal ridges or elevations.
Figure 6D:
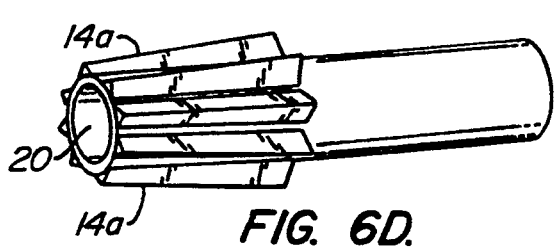
FIG. 6D shows a side view of longitudinal ridge with a decreasing slope toward the body or base of the male organ.

Vacuum cylinder 2 may be supplied with a single ridge or a plurality of ridges or elevations 14 adapted to receive constrictor 4. See FIG. 6C. Elevation 14 is preferably longitudinal and multiple, although other configurations may be practical. Elevation 14 facilitates moving constrictor 4 from cylinder 2 to the male organ by decreasing the area of constrictor 4 applied to cylinder 2 and thus reducing the coefficient of friction. Cylinder 2 may be sloped or tapered towards proximal end 20 to further assist in sliding constrictor 4 onto the male organ. Alternatively, a plurality of longitudinal elevations 14a can be provided with a variation in thickness or slope to achieve the same effect. See FIG. 6D. Embodiments having both elevation 14 and hole 12 would preferably elevate hole 12 so that constrictor 4 blocks hole 12 while contacting elevation 14.

Another feature of the present invention is a vacuum gauge 26 which facilitates incremental increase of the vacuum. Alternatively, a vacuum gauge 26a could be attached to vacuum cylinder 2 directly. See FIG. 8. Sudden increase of vacuum may cause reflex vaso-constriction. This physiologic reflex, which could defeat the purpose of the vacuum, can be prevented by use of the vacuum gauge. Incremental vacuum application reduces the incidence of ecchymoses or petechiae which tend to occur with sudden vacuum application.

An additional use of vacuum gauge 26 is that any undesired slow leakage of the vacuum pressure can be compensated for by activation of the pump (not shown) to maintain a steady vacuum pressure. This is a desirable feature because the seal between vacuum cylinder 2 and the body is imperfect due to the anatomy of the area and the presence of hair. Although a lubricant is used as a seal, slows leakage of the vacuum generally occurs. Thus, inclusion of vacuum gauge 26 in the system allows for accurate compensation of this leakage from the imperfect seal and it allows for reproducible results for the user.

Further, vacuum gauge 26 helps to prevent excess vacuum pressure, which could be damaging. The use of a vacuum device to produce an erection-like state requires a learning curve by the user. Vacuum gauge 26 provides visual feedback to facilitate the learning curve and diminishes frustration. It thus provides improved patient performance and compliance. Because a maximum of 300 to 350 mm Hg is recommended, the vacuum gauge is useful as a safety feature as well as for the other reasons mentioned. The usual vacuum pressure applied is about 200 mm Hg.

Another safety feature is a temperature display device, preferably a liquid crystal display (not shown). The LCD measures the surface temperature of the male organ before and after application of the device. Since surface temperature is in part a function of blood flow, this temperature sensing feature can be used for initial calibration as well as intermittent or constant monitoring of adequate blood flow. Some preselected temperature drop, i.e., 3° C., can be used as the appropriate end point or maximum temperature drop for safe use.

An additional use of the temperature sensor is provision of valuable diagnostic information. A ratio of core body temperature to organ surface temperature gives a rough measure of blood flow to the organ. This temperature index is particularly useful when combined with the index provided by the ratio between the brachial arterial blood pressure and the organ blood pressure. Additionally, following use of the device, there is often a reactive increase in surface temperature of the male organ. That is, increased blood flow post-use suggests normal pliability of the arteries. The use of the above three observations can substitute inexpensively for male organ plethysmography which is an expensive modality for the diagnosis of impotence.

A number of variations of the invention will be apparent to those of ordinary skill in the art. For instance, other connecting means could be used instead of the tucking the knot under a turn in the constrictor. Examples include VELCRO TM, a hook and eye, and a snap-on or bullet connector. Also, a displacement tube could be positioned slidably over the vacuum cylinder and sized to push the constrictor off the vacuum cylinder and onto the base of the male organ. Additionally, all or selected parts of at least one surface of the constrictor could be rendered rough in texture to facilitate frictional adherence of the secured constrictor. Thus, the present invention is not limited by the description of its preferred embodiment, but rather by the scope of the following claims.

What is claimed is:

1. An improved device to produce or maintain a male erection-like state with a vacuum-generating apparatus, said improved device comprising:
    a cylinder coupled to the vacuum-generating apparatus at one end and adapted to receive a male sex organ at another end to initiate an engorgement of the male sex organ;
    an elongated constrictor positioned on an exterior surface of the cylinder, said elongated constrictor
        formed from an elastomeric material having a generally linear configuration when not in use,
        dimensioned to provide a plurality of turns around the cylinder,
        slidable from the cylinder to the base of the male sex organ, and
        adapted to constrictively contact a base of the male sex organ to maintain engorgement therein,
        wherein said constrictor includes a bulge positioned to assist with retention of the constrictor when the constrictor is in contact with the male sex organ.

2. A device of claim 1 wherein the elongated constrictor includes a length calibration marking.

3. A device of claim 1 in which the elongated constrictor is formed from a length of latex surgical tubing which is approximately one-eighth inch thick.

4. A device of claim 1 wherein the bulge includes a knot.

* * * * *